United States Patent [19]

de Vries et al.

[11] Patent Number: 4,668,231
[45] Date of Patent: May 26, 1987

[54] IMPLANTABLE HAND-OPERABLE DISPENSERS FOR FLUID MEDICAMENTS

[75] Inventors: Gerrit de Vries, WE Roden; Jozef G. M. Leuveld, TA Leek; Johan W. Kleijn, WG Roden, all of Netherlands

[73] Assignee: Cordis Corporation, Miami, Fla.

[21] Appl. No.: 696,772

[22] Filed: Jan. 31, 1985

[30] Foreign Application Priority Data

Feb. 15, 1984 [NL] Netherlands .................. 8400489

[51] Int. Cl.$^4$ .............................. A61M 1/00
[52] U.S. Cl. .................... 604/891; 604/153
[58] Field of Search .................... 604/8–10, 604/175, 181, 183, 185, 186, 891, 151–153, 141

[56] References Cited

U.S. PATENT DOCUMENTS

| | | | |
|---|---|---|---|
| 3,503,402 | 3/1970 | Schulte | 604/9 |
| 3,692,027 | 9/1972 | Ellinwood, Jr. | |
| 3,768,508 | 10/1973 | Schulte | 604/9 |
| 3,827,439 | 8/1974 | Schulte et al. | |
| 3,951,147 | 4/1976 | Tucker et al. | |
| 3,976,402 | 8/1976 | Lundquist | 604/152 |
| 4,013,074 | 3/1977 | Siposs | |
| 4,056,095 | 11/1977 | Rey et al. | 604/891 |
| 4,146,029 | 3/1979 | Ellinwood, Jr. | 604/891 |
| 4,152,098 | 5/1979 | Moody et al. | |
| 4,193,397 | 3/1980 | Tucker et al. | |
| 4,196,747 | 4/1980 | Quigley et al. | 604/247 |
| 4,221,219 | 9/1980 | Tucker | |
| 4,346,704 | 8/1982 | Kulle | 604/247 |
| 4,354,492 | 10/1982 | McPhee | 604/247 |
| 4,487,603 | 12/1984 | Harris | 604/891 |
| 4,544,371 | 10/1985 | Dormandy, Jr. et al. | 604/891 |
| 4,548,607 | 10/1985 | Harris | 604/891 |

FOREIGN PATENT DOCUMENTS

| | | |
|---|---|---|
| 68815 | 5/1983 | European Pat. Off. . |
| 7901461 | 2/1979 | Netherlands . |
| 2028275 | 5/1980 | United Kingdom . |

Primary Examiner—C. Fred Rosenbaum
Assistant Examiner—Gene B. Kartchner
Attorney, Agent, or Firm—Lockwood, Alex, Fitzgibbon & Cummings

[57] ABSTRACT

YA hand-operable dispenser for fluid medicaments is provided in a form which is suitable for implanting same within a human body which permits controlled and convenient dispensing of fluid medicament to a desired somewhat remote location within the body. Propelling assemblies and blocking assemblies are provided and positioned so that they cooperate with each other along a medicament flow channel within the device in order to provide a controlled dispensing of a unit dose of medicament to the desired remote location. The medicament flow channel includes a blocking assembly at its downstream end.

19 Claims, 4 Drawing Figures

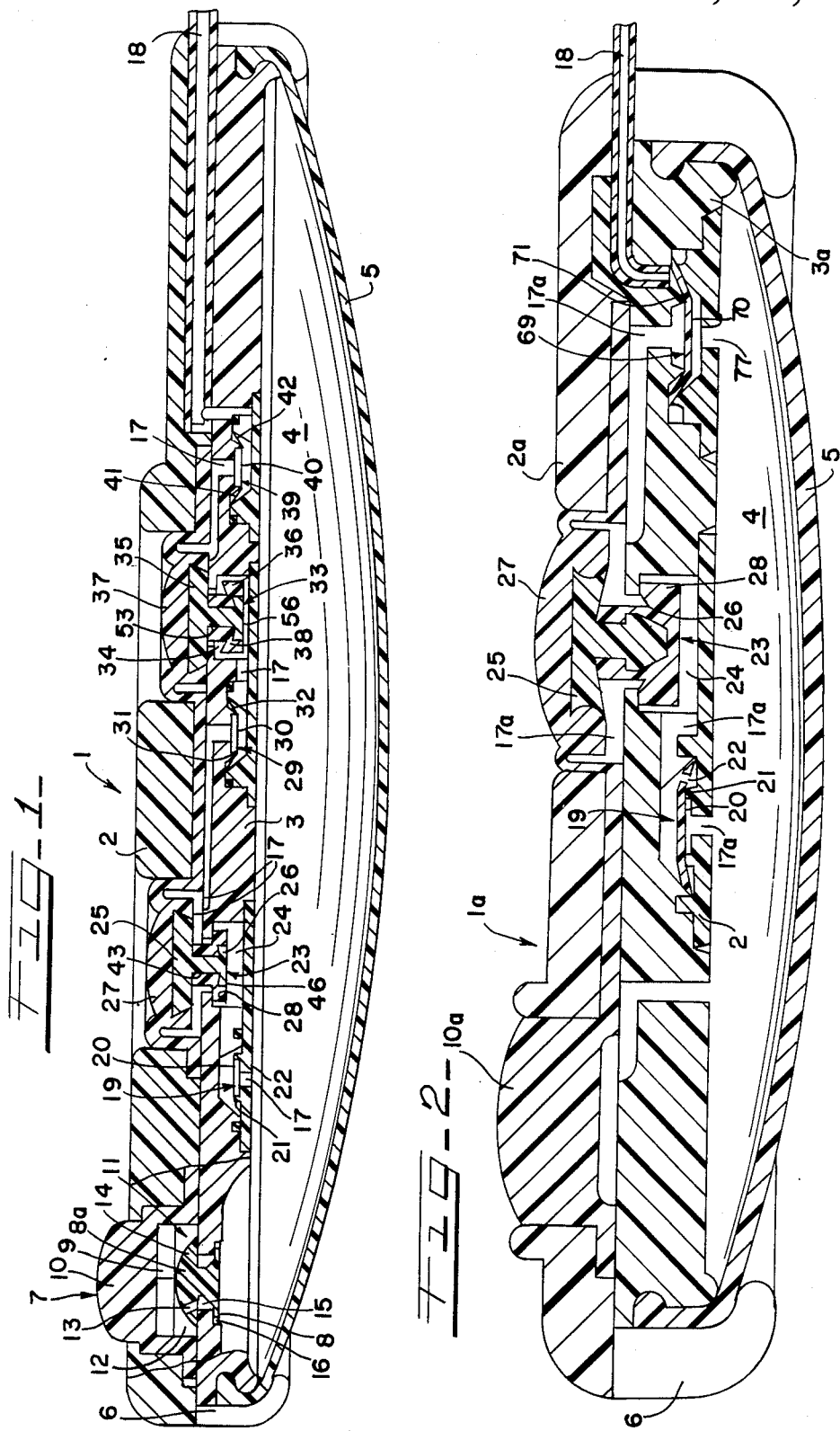

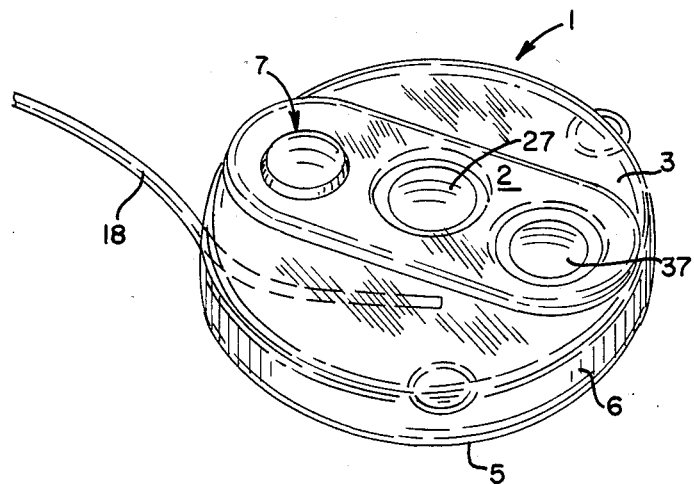
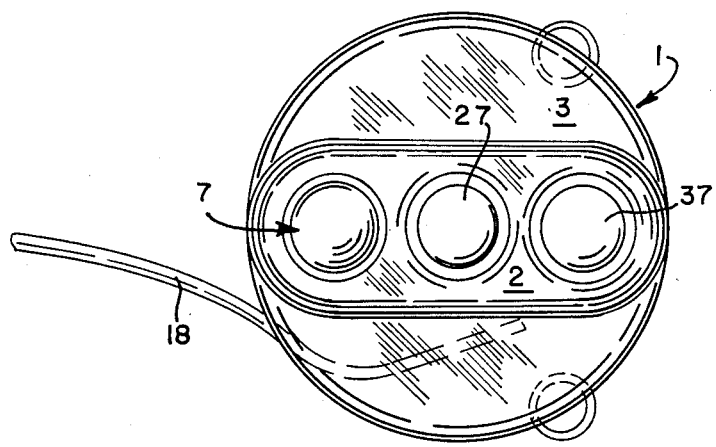

IMPLANTABLE HAND-OPERABLE DISPENSERS FOR FLUID MEDICAMENTS

DESCRIPTION

The invention generally relates to hand-operable dispensers for fluid medicaments, more particularly to dispensers that are implantable within the human body and that are constructed such that at least all of the parts thereof which, when implanted, contact internal portions of the body are made of a biocompatible material. Dispensers according to this invention include medicament propelling means and blocking means which cooperate with each other along a medicament flow channel within the device in order to provide controlled medicament flow therethrough to an outlet conduit which directs medicament to the desired location within the body.

Sufferers from certain diseases, for example those patients that experience a great deal of pain, may benefit from the dosed administration of a medicament such as a sedative directly to or in close proximity of the pain center. In this connection, it should be borne in mind, for that matter, that pain centers may be located deep within the body, and the local administration of medication thereto typically involves a liquid medicament and requires means to transport the medicament to such an internal body location. Sometimes such administration involves a hypodermic syringe and needle and/or the services of a trained medical professional. Many patients will consider it advantageous if the dosage of such a liquid medicament could be safely and conveniently self-administered.

A particularly important consideration is that any device or dispenser of medicament that has self-administration capabilities should also include means to safeguard against accidental or unintentional administration of the medicament. Another important consideration of self-administered medicament dispensers is that the medicament should be dispensed in quantities of known unit dosages. Furthermore, because liquid medicaments such as many sedatives are highly viscous, various dispensers that have been utilized or proposed heretofore for dispensing same are unsatisfactory since they include pivoting members, floating parts, or both that clog or stick after a period of use.

The present invention provides dispensers for fluid medicaments that have structural features which permit the safe, controlled and convenient self-administration of unit dosages of fluid medicaments, which structural features avoid the use of components that pivot or float and that would tend to malfunction or easily plug up. Devices according to this invention are implantable, self-administered dispensers that include a body or casing having a flexible-walled reservoir assembled thereonto, a one-way filler or supply port assembly mounted on the casing and communicating with the reservoir, a connecting channel having a plurality of channel segments within the body, one such channel segment providing fluid passage communication between the reservoir and a one-way valve assembly. Positioned along a downstream segment of the connecting channel is a propelling assembly that advances fluid medicament through this channel section. A blocking assembly is also provided within a section of the connecting channel in order to permit, in cooperation with the propelling assembly, the controlled flow of fluid through the connecting channel and to an outlet from the device while, when dispensing is not desired, preventing fluid flow therethrough. A dosage of medicament is dispensed when the patient manipulates a portion of the propelling assembly that is accessible through the casing of the implanted device. The blocking assembly and propelling assembly cooperate to selectively open and close the connecting channel in order to permit, only when desired, the propelled passage of a dosage of medicament out of the device and through a delivery tube that opens at the location where the medicament is to be delivered.

It is accordingly a general object of the present invention to provide an implantable hand-operable dispenser for fluid medicaments.

Another object of this invention is to provide an improved implantable medicament dispenser that permits the patient to safely and conveniently self-administer a medicament fluid, even one which is highly viscous.

Another object of this invention is to provide a self-administration fluid medicament dispenser that dispenses a unit dosage of the medicament in response to only deliberate and knowing actions by the person administering the medicament.

These and other objects of the present invention will be apparent from the following description of the invention, taken in conjunction with the accompanying drawings, wherein:

FIG. 1 is a cross-sectional view through the preferred medicament dispenser according to this invention that requires serial activation of two distinct propelling assemblies in order to dispense fluid therefrom;

FIG. 2 is a cross-sectional view through another embodiment of the medicament dispenser according to this invention which dispenses the fluid by manipulating a single activation site;

FIG. 3 is a perspective view of the medicament dispenser shown in FIG. 1; and

FIG. 4 is a top plan view of the medicament dispenser shown in FIG. 1.

The dispensing means illustrated in FIGS. 1, 3 and 4, generally designated by reference numeral 1, has a casing which typically includes an upstanding component 2 and a body component 3, both of which are made of a relatively rigid, biocompatible polymeric material. Polyethyl sulfone is an exemplary biocompatible material that is suitable in this regard. Jpstanding component 2 and body component 3 are provided as integrally molded units or are secured together and/or to each other by appropriate means such as ultrasonic sealing or structures which provide fixed connections such as adhesives or screws.

A reservoir 4 is partly defined by a yielding wall 5 that is secured to the body component 3 by suitble means such as the illustrated snap-on ring 6 which provides a tight-sealing assembly of the periphery of the yielding wall 5 to the body component 3. Reservoir 4 is further defined by the underside of the body component 3. Yielding wall 5 is structured and fabricated of a material such that it insures that the liquid contents of the reservoir substantially fill the reservoir 4 even as the liquid medicament confined thereby is dispensed out of the reservoir 4. In other words, as each unit dose of liquid medicament is withdrawn from the reservoir 4, the yielding wall 5 is displaced toward the body component 3 in order to maintain close confinement of the medicament remaining within the reservoir 4 so that the medicament therewithin is maintained under a substantially constant pressure and so that air pockets are not developed therewithin. Yielding wall 5 is, for example, suitably made of a silicone rubber material that is reinforced with polyester fibers.

The entire dispensing device is designed to be suitable for and to be operative under conditions that obtain when such a device is implanted under the skin of a patient. In this regard, a supply port assembly, generally designated by reference numeral 7, provides a pathway through which the liquid medicament can be inserted into the reservoir 4 from outside of the patient's body, typically by means of a hypodermic needle device. Supply port assembly 7 includes a generally mushroom-shaped shut-off valve, generally designated by reference numeral 11, a needle stop plate 9 of generally known construction, and a domed pad 10 that projects above the upstanding component 2 of the device 1 in order to assist in the accurate location thereof when the device is implanted within the patient. Supply port assembly 7 further includes a chamber 12 that is recessed within the domed pad 10. The needle stop plate 9 and an extending cap 8a of the mushroom-shaped shutoff valve 11 are both disposed within the chamber 12. Channels 13 and 14 are provided through the extending cap 8a of the mushroom-shaped shutoff valve 11, which channels 13 and 14 communicate the chamber 12 with an annular space 15 located between the extending cap 8a and an extending foot 8 of the shutoff valve 11. Preferably, the space 15 is countersunk to form a disk-shaped space 16 which receives the extending foot 8.

Mushroom-shaped shutoff valve 11 is sized and structured such that its extending foot 8, under at-rest conditions, is sealingly positioned within the disk-shaped space 16, so as to prevent passage of liquid across the shutoff valve 11, particularly between the chamber 12 and the reservoir 4. Reservoir 4 is filled by inserting the needle of a hypodermic syringe filled with medicament through the domed pad 10, thereby engaging the substantially rigid stop plate 9 (made, for example, of a polysulfone). The stop plate 9 in turn pushes on the extending cap 8a of the shutoff valve 11 which, because it is made of a resilient material such as a silicone rubber, is deformed and pushed inwardly until the extending foot 8 is pushed away from its engagement with the disk-shaped space 16. When the plunger of the hypodermic needle is depressed and the liquid medicament flows out of the needle, the liquid medicament flows, by way of a slit-shaped space adjacent to the side wall of the needle stop plate 9, into the chamber 12, through channels 13 and 14, through the spaces 15 and 16, and into the reservoir 4. After the hypodermic needle is withdrawn from the domed pad 10, the domed pad 10 seals itself automatically in accordance with well-known self-sealing port principles, and the needle stop plate 9 returns to its at-rest position, which permits the mushroom-shaped shutoff valve 11 likewise to return to its at-rest position and original shape in order to once again block the passage of liquid between the chamber 12 and the reservoir 4.

A connecting channel 17 having a plurality of channel segments traverses a path that ultimately provides fluid-passing communication between the reservoir 4 and a delivery tube 18. Preferably, delivery tube 18 is made of a material that incorporates a contrast medium, so that the guiding of the delivery tube 18 to the site of treatment can be monitored by well-known X-ray techniques. Silicone rubber tubes incorporating such a contrast medium are suitable in this regard.

With more particular reference to connecting channel 17, an initial channel segment thereof provides a passageway between the reservoir 4 and a one-way valve assembly, generally designated by reference numeral 19, which includes a diaphragm 20, typically made of a resilient material such as silicone rubber, which, when the device is at rest, is in sealing engagement with a collar 21. Diaphragm 20 includes an aperture 22 through which liquid medicament may pass when the diaphragm 20 is moved by appropriate liquid pressures out of full sealing engagement with the collar 21.

The next channel segment of connecting channel provides a passageway to a recessed housing or chamber 24 within the body component 3, within which recessed chamber 24 is slidably mounted a portion of a blocking assembly, generally designated by reference numeral 23. Blocking assembly 23 includes a plunger assembly for selectively opening and closing the recessed housing 24 to a further channel segment of the connecting channel 17 which is downstream of the blocking assembly 23. The illustrated plunger assembly of the blocking assembly 23 includes a pushbutton 25 (for example made of a polysulfone), a resilient sealing sleeve 26 (for example made of a silicone rubber) and a resilient pad 27 (for example made of a silicone rubber) into which the top portion of the pushbutton 25 is imbedded. Resilient pad 27 is structured so that the plunger assembly is loaded or biased such that, when the device is at rest, a corner edge 28 of the sealing sleeve 26 engages a surface of the recessed chamber 24, thereby closing communication between the recessed chamber 24 and the segment of the connecting channel 17 which is present when the blocking assembly 23 is in its illustrated at-rest position. Preferably, the top surface of the resilient pad 27 is countersunk with respect to the outside surface of the upstanding casing component 2.

Another one-way valve assembly, generally designated by reference numeral 29, is interposed between the previously described segment of the connecting segment 17 and a further downstream segment thereof. One-way valve assembly 29, which is structured to be substantially the same as one-way valve assembly 19, includes a diaphragm 30 sealingly mounted onto a collar 31. Diaphragm 30 includes an aperture 32. Downstream of the further segment of the connecting channel 17 is another blocking assembly, generally designated by reference numeral 33, which blocking assembly 33 is similar to blocking assembly 23, except for one important difference. Blocking assembly 33 is biased or loaded, by the configuration and sizing of its resilient pad 37, in a generally downwardly oriented position at which the bottom or inside surface of its pushbutton 35 engages the body component 3 in order to preclude the formation of a channel segment therebetween.

A recessed chamber 34 within the body component 3 receives the lower portion of the pushbutton 35 and its sealing sleeve 36. When fluid pressure is suitably developed, the blocking assembly 33 moves upwardly until a corner edge 38 of the sealing sleeve 36 closes the recessed chamber 34, at which time a segment of the connecting channel 17 is formed between the upper surface of the body component 3 and the inside bottom surface of resilient pad 37 and the head of pushbutton 35. Thus formed connecting segment, when present, communicates with a terminal section of the connecting channel 17, which opens to another one-way valve assembly, generally designated by reference numeral 39. When open, one-way valve assembly 39 communicates with the delivery tube 18. One-way valve assembly 39 includes a diaphragm 40 in sealing engagement with a collar 41 when the device is at rest. Diaphragm 40 includes an aperture 42.

In FIG. 1, the medicament dispensing device is shown in its at-rest or quiescent state at which it is in a non-dispensing mode. Each of the one-way valve assemblies 19, 29 and 39 are closed, and the blocking assembly 23 functions as a plunger in its uppermost or outwardly extending position, while the blocking assembly 33 functions as a plunger in its lowermost or inwardly directed position at which the corner edge 38 thereof is spaced from the body component 3. When it is desired to dispense a unit dosage of fluid medicament into and through the delivery tube 18, with fluid filled within the connecting channel 17, the user first depresses the blocking assembly 23, which propels fluid medicament that will raise or outwardly extend the blocking assembly 33. Dispensing is carried out when the thus outwardly extended blocking assembly 33 is depressed to return to its inwardly directed at-rest orientation which is the orientation shown in FIG. 1. Thus, the blocking assembly 33 functions as a means for propelling the fluid through the terminal section of the connecting channel 17 and through the delivery tube 18.

With more particular reference to the steps by which liquid medicament passes through each segment of the connecting channel 17, the following sequence of events occurs. When the blocking assembly 23 is depressed, the pushbutton 25 and its sealing sleeve 26 move downwardly, thereby releasing the seal between the corner edge 28 and the recessed housing 24. Such depressing of the blocking assembly 23 causes the blocking assembly 23 to function as a plunger whereby fluid in the recessed housing 24 exerts pressure on the diaphragm 20 of the one-way valve assembly 19 to thereby safeguard the maintenance of the seal between the diaphragm 20 and its collar 21. At the same time, a metered quantity of liquid medicament is forced from the recessed housing or chamber 24 by movement of the pushbutton 25 and its sealing sleeve 26 into the recessed chamber 24, which displaces medicament generally upwardly through the blocking assembly 23 and to the next downstream segment of the connecting channel 17 toward the one-way valve assembly 29.

This downstream displacement of fluid and simultaneous exertion of pressure on the diaphragm 20 of the one-way valve assembly 19 in order to maintain same in a closed state is facilitated by providing a spacing between bottom surface 46 of the blocking assembly 23, which is achieved in part by appropriately sizing the length of stem 43 of the pushbutton 25. This downstreamwardly directed pressure is imparted to liquid medicament already in the downstream section of connecting channel 17, which in turn exerts pressure on the diaphragm 30 of the one-way valve assembly 29, this in turn causing a lifting of the diaphragm 30 off of its collar 31, whereby the liquid medicament within this downstream section of the connecting channel 17 flows through aperture 32, then through the further downstream segment of the connecting channel 17, and into the recessed chamber 34 of the blocking assembly 33.

At this stage, the liquid medicament flowing through aperture 32 exerts a hydraulic force on the bottom surface 56 of the blocking assembly 33, which in turn raises the blocking assembly 33. This activity is assisted by providing spacing between the bottom surface 56 of the blocking assembly 33 and the opposing wall of the recessed chamber 34, which is accomplished by appropriately sizing stem 53 of the pushbutton 35. Blocking assembly 33 is thereby displaced upwardly or outwardly through a distance that is substantially equal to that through which the blocking assembly 23 is displaced inwardly when pressed by the user, such being achieved by providing generally equal volumeric respective sizings of the blocking assembly 23 and of the blocking assembly 33, their respective recessed chambers 24 and 34, so that the entire incremental volume of liquid medicament that is displaced from chamber 24 by depressing the blocking assembly 23 is received in the recessed chamber 34, at which time the recessed chamber 34 is sealed when the corner edge 38 engages the upper or outwardly directed surface of the recessed chamber 34.

If appropriate safeguards are not taken, the outward or upward displacement of fluid medicament through the blocking assembly 33 could result in opening of the one-way valve assembly 39, which would permit a somewhat uncontrolled and non-incremental volume of liquid medicament to flow through the aperture 42 and into the delivery tube 18. Although this undesirable result should cease when the corner edge 38 seals off the recessed chamber 34, this possibility is preferably prevented by designing the one-way valve assembly 39 such that the pressure that is required to lift the diaphragm 40 off of its collar 41 is greater than the pressure required to displace the blocking assembly 33 outwardly or upwardly. Moreover, this pressure required to open the one-way valve assembly 39 is less than that which is developed when the blocking assembly 33 is depressed. In other words, the hydraulic pressure generated by depressing the blocking assembly 33 is of such a high value that it lifts the diaphragm 40 off of its collar 41 to permit an incremental unitary dosage amount of liquid medicament to flow through the aperture 42, into the delivery tube 18 and to the site where the fluid medicament is to be administered.

With further reference to the blocking assembly 23, when same is depressed, it moves until the pushbutton 25 engages the body component 3. As soon as the blocking assembly 23 is released, the pushbutton 25 moves upwardly or outwardly to return to its at-rest position by virtue of the loaded or biased attributes of the resilient pad 27 which had been deformed during depression of the blocking assembly 23. As a result of this return to the upward or outward orientation, the spacing between the bottom surface 46 and the opposing wall of the recessed chamber 24 increases to thereby lift the diaphragm 20 until the moment when the corner edge 28 has again reached the position shown in FIG. 1 and recessed chamber 24 is again closed. During the time that the diaphragm 20 is lifted off of its collar 21, medicament flows from the reservoir 4 and through the aperture 22 of the one-way valve assembly 19, this flow being assisted by the collapsibility and flexibility of the yielding wall 5 such that the volume of the reservoir 4 is reduced as the yielding wall 5 collapses when the medicament passes through the one-way valve assembly 19 while the device is implanted and in contact with the patient.

From the preceding, it is clear that the dosage of a metered quantity of a liquid medicament will be dispensed out of the delivery tube 18 only after the device according to this embodiment is subjected to two distinct manipulations. First, blocking assembly 23 must be depressed, which results in the raising or outward extension of the blocking assembly 33. Then, in order for the medicament to be dispensed, a second distinct step must performed, which second step is the depression of the blocking assembly 33. This provides a built-in security factor which substantially eliminates the possibility of an inadvertent dosage of medicament being dispensed through the delivery tube 18.

With reference to the embodiment illustrated in FIG. 2, this device 1a includes only a single blocking assembly 23 which performs a dual function of providing blocking attributes while also functioning as means for propelling liquid medicament through the delivery tube 18, when such delivery is desired. Device 1a also includes a domed pad 10a projecting above upstanding component 2a providing a relatively simple construction for filling the reservoir 4 by passing a hypodermic needle therethrough. Also included is the one-way valve assembly 19 and a further one-way valve assembly 69 which does not have an aperture through its diaphragm, valve assemblies 19 and 69 being within body component 3a.

The at-rest or quiescent state of device 1a is illustrated in FIG. 2, this being the position of all components of the device 1a between the times at which medicament dispensing is desired. More particularly, the blocking assembly 23 is in its upward or outwardly extending position at which the corner edge 28 of the sealing sleeve 26 sealingly engages the outwardly extending wall of the recessed chamber 24. When it is desired to supply a dose of medicament through the delivery tube 18, pressure is exerted on the pushbutton 25 through the resilient pad 27 of the blocking assembly 23 in order to depress same and remove the sealing engagement between the corner edge 28 and the recessed chamber 24. Because liquid medicament is included within the section of the connecting channel 17a which is between the blocking assembly 23 and the one-way valve assembly 19, the diaphragm 20 is forced onto its collar 21 in order to prevent passage of liquid medicament through its aperture 22. On the other hand, this same depression of the blocking assembly 23 exerts pressure on the section of the connecting channel 17a between the blocking assembly 23 and the one-way valve assembly 69 which results in the lifting of its diaphragm 70 off of its collar 71, whereby the liquid medicament flows through the thus formed opening between the collar 71 and the diaphragm 70 and into the delivery tube 18.

When the depressed blocking assembly 23 is released, it will return to its upward or outwardly extending orientation as illustrated in FIG. 2, which upward movement creates a lowered pressure for fluid sealed within the blocking assembly 23 so as to cause a slight reverse flow of fluid medicament which results in a sealing of the diaphragm 70 against its collar 71. Simultaneously, this return movement of the blocking assembly 23 to its upward or outwardly extending orientation opens an additional volume within the recessed chamber 24, in response to which liquid medicament flows, thereby lifting the diaphragm 20 off of its collar 21 and flowing liquid medicament through the aperture 22 from the reservoir 4 in order to thereby refill the recessed chamber 24.

A channel 77 is provided for liquid pressure communication between the reservoir 4 and the diaphragm 70 of the one-way valve assembly 69. Aperture free diaphragm 70 is structured and positioned so that liquid medicament cannot flow therethrough from the channel 77. An increase in pressure caused by an increase in pressure on the outside surface of the reservoir 4 will enhance the seating of the diaphragm 70 onto its collar 71 in order to ensure that, if such outside pressure is increased onto the implanted reservoir 4, such increase will not cause medicament to be dispensed through the delivery tube 18.

It is to be appreciated that modifications can be made to the dispensing device as described hereinabove and as shown in the drawings without departing from the scope of this invention.

We claim:

1. An implantable, manually operable dispenser for a fluid medicament, comprising;
    (a) a body member having reservoir means for storing a fluid medicament, said reservoir means having a flexible wall that expands and collapses as fluid medicament flows respectively into and out of the reservoir means;
    (b) a supply port assembly on said body member, said supply port assembly being in fluid-passing communication with said reservoir means;
    (c) a connecting channel within said body member, said connecting channel having a section thereof that is in fluid-passing communication with said reservoir means and another section thereof that is in fluid-passing communication with a delivery tube outlet from said body member;
    (d) propelling means within said connecting channel for advancing fluid medicament in a downstream direction through said connecting channel toward said delivery tube outlet;
    (e) one-way blocking means within said connecting channel for permitting, in cooperation with activation of said propelling means, controlled fluid flow therethrough toward said delivery tube outlet, said one-way blocking means also being for preventing fluid flow therethrough toward said delivery tube outlet when said propelling means is not activated; and
    wherein said blocking means includes a diaphragm that is tensioned when there is no pressure differential thereacross and that sealingly engages a collar of the body member, and wherein said diaphragm has an aperture therethrough.

2. The implantable dispenser according to claim 1, further including another controlled-flow blocking means positioned within a segment of the connecting channel that is between said propelling means and said reservoir means.

3. The implantable dispenser according to claim 1, wherein a plurality of blocking means are provided so as to be both upstream and downstream of said propelling means.

4. The implantable dispenser according to claim 3, further including a plurality of said propelling means having blocking means both upstream and downstream thereof.

5. The implantable dispenser according to claim 1, further including three blocking means and two propelling means that are alternately located with respect to each other within the connecting channel.

6. The implantable dispenser according to claim 1, wherein the propelling means includes sealing means for blocking the flow of fluid therethrough when said propelling means is at its inwardly directed, depressed position and when said propelling means is at its outwardly directed, extended position.

7. An implantable, manually operable dispenser for a fluid medicament, comprising;
   (a) a body member having reservoir means for storing a fluid medicament, said reservoir means having a flexible wall that expands and collapses as fluid medicament flows respectively into and out of the reservoir means;
   (b) a supply port assembly on said body member, said supply port assembly being in fluid-passing communication with said reservoir means;
   (c) a connecting channel within said body member, said connecting channel having a section thereof that is in fluid-passing communication with said reservoir means and another section thereof that is in fluid-passing communication with a delivery tube outlet from said body member;
   (d) propelling means within said connecting channel for advancing fluid medicament in a downstream direction through said connecting channel toward said delivery tube outlet;
   (e) one-way blocking means within said connecting channel for permitting, in cooperation with activation of said propelling means, controlled fluid flow therethrough toward said delivery tube outlet, said one-way blocking means also being for preventing fluid flow therethrough toward said delivery tube outlet when said propelling means is not activated, and said blocking means includes a diaphragm that is tensioned when there is no pressure differential thereacross and that sealingly engages a collar of the body member; and
   wherein said propelling means includes plunger means for reciprocatingly opening and closing a chamber of the body member through which said plunger means is mounted.

8. The implantable dispenser according to claim 1, wherein the body member includes a plurality of said propelling means for metering and displacing substantially equal quantities of liquid medicament, and another blocking means is provided between said plurality of propelling means.

9. The implantable dispenser according to claim 1, wherein said propelling means includes a pushbutton having a stem extending into a chamber of the body member, and resilient means mounted to said stem for sealingly engaging and closing said chamber when said pushbutton is at its outwardly directed, extended position.

10. The implantable dispenser according to claim 9, wherein said propelling means further includes a resilient pad to which said pushbutton is mounted, said resilient pad providing means for biasing said propelling means to said sealing engagement and closing of said chamber.

11. The implantable dispenser according to claim 8, wherein the blocking means closest to said outlet from the body member is structured for opening at a pressure greater than pressure needed for outwardly moving the propelling means most closely spaced therefrom.

12. The implantable dispenser according to claim 1, wherein said supply port assembly includes one-way means for shutting off flow between said supply port assembly and said reservoir means.

13. The implantable dispenser according to claim 12, wherein said one-way means includes a resilient mushroom-shaped member mounted within a passageway space through said body member, said resilient mushroom-shaped member including an extending foot partially defining said reservoir means and including an extending cap opposite of said extending foot, said extending cap having a channel therethrough.

14. The implantable dispenser according to claim 13, wherein said supply port assembly further includes a needle stop plate movable toward and away from said extending cap of the mushroom-shaped member, and a domed pad covers said needle stop plate.

15. An implantable, manually operable dispenser for a fluid medicament, comprising;
   (a) a body member having reservoir means for storing a fluid medicament, said reservoir means having a flexible wall that expands and collapses as fluid medicament flows respectively into and out of the reservoir means;
   (b) a supply port assembly on said body member, said supply port assembly being in fluid-passing communication with said reservoir means;
   (c) a connecting channel within said body member, said connecting channel having a section thereof that is in fluid-passing communication with said reservoir means and another section thereof that is in fluid-passing communication with a delivery tube outlet from said body member;
   (d) propelling means within said connecting channel for advancing fluid medicament in a downstream direction through said connecting channel toward said delivery tube outlet;
   (e) one-way blocking means within said connecting channel for permitting, in cooperation with activation of said propelling means, controlled fluid flow therethrough toward said delivery tube outlet, said one-way blocking means also being for preventing fluid flow therethrough toward said delivery tube outlet when said propelling means is not activated;
   (f) a plurality of blocking means are provided so as to be both upstream and downstream of said propelling means, wherein said blocking means downstream of the propelling means includes a diaphragm that is tensioned when there is no pressure differential thereacross and that sealingly engages a collar of the body member; and
   (g) means are provided for transmitting fluid pressure within said reservoir means to said tensioned diaphragm and for sealingly engaging said tensioned diaphragm onto its said collar.

16. The implantable dispenser according to claim 8, wherein the propelling means that is most downstream includes resilient means mounting a pushbutton of the propelling means to said body member, said resilient means biasing said pushbutton in a depressed orientation, and wherein upstream propelling means includes resilient means mounting a pushbutton of the propelling means to said body member, said resilient means biasing said pushbutton in an outwardly extended orientation.

17. An implantable, manually operable dispenser for a fluid medicament, comprising;
   (a) a body member having reservoir means for storing a fluid medicament, said reservoir means having a flexible wall that expands and collapses as fluid medicament flows respectively into and out of the reservoir means;

(b) a supply port assembly on said body member, said supply port assembly being in fluid-passing communication with said reservoir means;

(c) a connecting channel within said body member, said connecting channel having a section thereof that is in fluid-passing communication with said reservoir means and another section thereof that is in fluid-passing communication with a delivery tube outlet from said body member;

(d) propelling means within said connecting channel for advancing fluid medicament in a downstream direction through said connecting channel toward said delivery tube outlet;

(e) one-way blocking means within said connecting channel for permitting, in cooperation with activation of said propelling means, controlled fluid flow therethrough toward said delivery tube outlet, said one-way blocking means also being for preventing fluid flow therethrough toward said delivery tube outlet when said propelling means is not activated; and (f) another controlled-flow blocking means positioned within a segment of the connecting channel that is between said propelling means and said reservoir means, wherein said blocking means between the propelling means and the reservoir means includes a diaphragm that is tensioned when there is no pressure differential thereacross and that sealingly engages a collar of the body member, and wherein said diaphragm has an aperture therethrough.

18. The implantable dispenser according to claim 1, wherein said propelling means includes plunger means for reciprocatingly opening and closing a chamber of the body member in communication with said connecting channel.

19. The implantable dispenser according to claim 16, wherein said downstream propelling means and said upstream propelling means are in fluid-passing communication through a segment of said connecting channel, whereby depression of said upstream propelling means outwardly extends said downstream propelling means.

* * * * *